United States Patent [19]

Darnell et al.

[11] Patent Number: 5,230,801
[45] Date of Patent: Jul. 27, 1993

[54] RECOVERY OF ALCOHOLS FROM N-PARAFFINS BY PERVAPORATION

[75] Inventors: Charles P. Darnell; Russell J. Koveal; Tan J. Chen, all of Baton Rouge, La.; W. S. Winston Ho, Annandale, N.J.

[73] Assignee: Exxon Research and Engineering Company, Florham Park, N.J.

[21] Appl. No.: 971,024

[22] Filed: Nov. 2, 1992

[51] Int. Cl.⁵ .................................. B01D 15/00
[52] U.S. Cl. ........................... 210/640; 210/651; 210/653; 210/500.38; 585/818; 568/913
[58] Field of Search ........... 210/640, 651, 653, 500.38, 210/500.38, 500.27; 55/16; 585/818; 568/913, 697; 208/103

[56] References Cited

U.S. PATENT DOCUMENTS

| | | | |
|---|---|---|---|
| 4,547,530 | 10/1985 | McCreedy et al. | 521/139 |
| 4,652,343 | 3/1987 | Sridhar | 568/913 |
| 4,759,850 | 7/1988 | Farnand et al. | 210/654 |
| 4,774,365 | 9/1988 | Chen et al. | 568/697 |
| 4,876,403 | 10/1989 | Cohen et al. | 568/913 |
| 4,925,459 | 5/1990 | Rosey et al. | 585/818 |
| 4,925,562 | 5/1990 | Le Hennepe et al. | 210/640 |
| 4,944,880 | 7/1990 | Ho et al. | 210/500.39 |
| 4,960,519 | 10/1990 | Pasternak et al. | 210/640 |
| 4,971,699 | 11/1990 | Bartels | 210/640 |
| 4,990,275 | 2/1991 | Ho et al. | 210/500.39 |
| 5,039,418 | 8/1991 | Schucker | 210/640 |
| 5,156,790 | 10/1992 | Brüschke | 210/490 |

FOREIGN PATENT DOCUMENTS 2111888 9/1977 Japan.
2049903 3/1987 Japan.

Primary Examiner—Robert A. Dawson
Assistant Examiner—Ana M. Fortuna
Attorney, Agent, or Firm—Joseph J. Allocca

[57] ABSTRACT

The present invention is a process for the recovery of normal alcohols, especially $C_1$-$C_{20}$ n-alcohols, preferably n-$C_4$-$C_{14}$ alcohols, most preferably n-$C_6$-$C_{11}$ alcohols from n-paraffins by means of pervaporation through a membrane. The alcohols/paraffin feed mixture may be that produced in the Fischer-Tropsch synthesis process wherein mixtures of CO and $H_2$ are reacted to produce paraffin waxes and a minor but still valuable amount of alcohols.

6 Claims, 1 Drawing Sheet

RECOVERY OF ALCOHOLS FROM N-PARAFFINS BY PERVAPORATION

BACKGROUND OF THE INVENTION

1. Field of the Invention

The present invention is directed to a process for selectively removing normal $C_1$-$C_{20}$ alcohols, preferably normal $C_4$-$C_{14}$ alcohols, more preferably normal $C_6$-$C_{11}$ alcohols from mixtures of alcohols and paraffins by use of a membrane, preferably a polyester or polyester copolymer membrane under pervaporation conditions. The mixtures of alcohols and paraffins are typically the product of the Fischer-Tropsch process. In the Fischer-Tropsch process CO and $H_2$ are catalytically converted into paraffins and a small but still significant quantity of alcohol containing from 4 to 14 carbons. This valuable alcohol fraction is separated from the paraffin-alcohol mixture by selective permeation of the alcohol through a membrane under pervaporation conditions. Preferably the membrane employed is a polyimide/aliphatic polyester copolymer membrane.

2. Summary of the Invention

It has been discovered than n-alcohols, preferably n-$C_1$-$C_{20}$ alcohols especially normal $C_4$-$C_{14}$ alcohols, most preferably n-$C_6$-$C_{11}$ alcohols are separated from mixtures of said alcohols with n-paraffins by the selective permeation of the alcohol through a membrane, preferably a polyester containing membrane under pervaporation conditions. Typically the alcohol/paraffin stream is one obtained by the Fischer-Tropsch Process. In that process CO and $H_2$ are catalytically converted into paraffin waxes. A small but economically significant quantity of $C_4$-$C_{14}$ normal alcohols is also produced. The alcohol/paraffins feed mixture which is subjected to pervaporative membrane separation is that fraction boiling in the 65° to 450° C. range containing $C_1$ to $C_{20}$ alcohols, preferably in the 100° to 300° C. range, containing $C_4$ to $C_{14}$ alcohols.

The alcohol concentration in the alcohol/paraffins mixture can range between 0.5 to 99.5% alcohol, preferably 1 to 10% alcohol.

Pervaporation is a process run at generally high temperature, e.g., greater than 100° C., preferably greater than 160° C., and more preferably at even higher temperature and generally relies on vacuum on the permeate side to evaporate the permeate from the surface of the membrane and maintain the concentration gradient driving force which drives the separation process. The maximum temperatures employed in pervaporation will be those necessary to vaporize the components in the feed which one desires to selectively permeate through the membrane while still being below the temperature at which the membrane is physically damaged. While a vacuum may be pulled on the permeate side operation at atmospheric pressure on the permeate side is also possible and economically preferable. In pervaporation it is important that the permeate evaporate from the downstream side (permeate side) of the membrane. This can be accomplished by either decreasing the permeate pressure (i.e. pulling a vacuum) if the permeate boiling point is higher than the membrane operating temperature or by increasing the membrane operating temperature above the boiling point of the permeate in which case the permeate side of the membrane can be at atmospheric pressure. This second option is possible when one uses a membrane capable of functioning at very high temperature. In some cases if the membrane operating temperature is greater than the boiling point of the permeate, the permeate side pressure can be greater than 1 atmosphere. The stream containing the permeate is cooled to condense out the permeated product. Condensation temperature should be below the dew point of the permeate at a given pressure level.

The alcohol concentration in the permeate can be increased by recycling the permeate back to the process along with fresh feed or by running the permeation process as a staged pervaporation wherein the permeate from a first pervaporation stage of zone is used as feed in a second pervaporation stage or zone. Anywhere from 2 to 5 or more stages may be used depending on the economic constraints involved in employing the additional stages and on the degree of improvement in terms of alcohol content secured by using more than 2 or 3 stages.

It is preferred that the present separation is conducted at atmospheric permeate pressure in that this reduces or eliminates vacuum requirements and should simplify the design of the permeate section as well as the design of the separation elements. Operation at atmospheric pressure, however, requires the use of a membrane capable of operating at high temperature, temperatures above the feed boiling point.

The process employs a dense film, non-porous membrane, preferably a polyester-containing membrane.

Polyimide/aliphatic polyester copolymer membranes are examples of high temperature stable membranes which can be used in this separation. The membranes are thin and comprise polyimide segments and polyester segments, the polyimide being derived from a dianhydride having between 8 and 20 carbons and a diamine having between 2 and 30 carbons, and the polyester is a polyadipate, a polysuccinate, a polymalonate, a polyoxalate or a polyglutarate. Membranes of the type are described in U.S. Pat. No. 4,944,880 and U.S. Pat. No. 4,990,275.

Polyurethane and polyurea-urethane membranes preferably those containing polyester moieties may also be employed.

Suitable aromatic polyurea-urethane membranes are characterized by possessing a urea index, defined as the percentage of the total of urea and urethane groups that are urea, of at least about 20% but less than 100%, an aromatic carbon content of at least about 15 mole %, a functional group density of at least 10 per 100 grams of polymer, and a C=O/NH ratio of less than about 8 and are described in U.S. Pat. No. 4,914,064. Thin film composites of polyurea-urethane film on support backing can be prepared as taught in U.S. Pat. No. 4,837,054 and U.S. Pat. No. 4,861,628. U.S. Pat. No. 4,879,044 described anisotropic polyurea-urethane membranes.

Polyurethane and polyurea-urethane membranes described in U.S. Pat. No. 4,115,465 can also be used. If supported on thermally stable backings such as Teflon, as disclosed in U.S. Ser. No. 452,888 filed Dec. 19, 1989, then these non-aromatic polyurethane and polyurea-urethane membranes of U.S. Pat. No. 4,115,464 can be employed at elevated temperatures, in excess of 120° C.

Halogenated polyurethane membranes described in U.S. Pat. Nos. 5,028,685 and 5,093,003 can also be employed in the separation.

Polyurethane-imide membranes preferably those containing polyester segments, can also be used and are described in U.S. Pat. No. 4,929,358.

Ioscyanurate crosslinked polyurethane membranes preferably those containing polyester segments are also useable and are described in U.S. Pat. No. 4,929,357.

Other useful membranes are described in U.S. Pat. No. 4,976,868 which describes polyester membranes per se, such as membranes made of polyethylene terephthalate/cyclohexane-dimethanol terephthalate and U.S. Pat. Nos. 4,946,594 and 4,997,906 which describe a crosslinked copolymer membrane derived from an aliphatic polyester, a dianhydride and a diisocyanate.

New, multi-block copolymer membranes, preferably containing polyester segments, are also suitable for use and are described in the following:

U.S. Pat. No. 5,039,418 describes a membrane made of a multi-block polymer comprising a first prepolymer comprising an oxazolidone made by combining (A) an epoxy with (B) a diisocyanate in an A/B or B/A mole ratio ranging from about 2.0 to 1.05, chain extended with a second, compatible prepolymer selected from the group consisting of (a) an (A) diisocyanate combined with a monomer selected from the group consisting of (B) polyester, diamine and dianhydride or its corresponding tetraacid or diacid-diester, in an A/B mole ratio ranging from about 2.0 to 1.05, (b) an (A) dianhydride or its corresponding tetraacid or diacid-diester combined with a monomer selected from (b) epoxy, diisocyanate, polyester and diamine, in an A/B mole ratio ranging from about 2.0 to 1.05, and (c) an (A) diamine combined with a monomer selected from (B) epoxy, diisocyanate, and dianhydride or its corresponding tetraacid or diacid-diester, in an A/B mole ratio ranging from about 2.0 to 1.05 and mixtures thereof.

U.S. Pat. No. 5,039,422 describes a membrane made of a multi-block polymer comprising a first prepolymer urea made by combining (A) diisocyanate with (B) diamine in an A/B or B/A mole ratio ranging from about 2.0 to 1.05, chain extended with a second, different compatible prepolymer selected from (a) an (A) dianhydride or its corresponding tetraacid or diacid-diester combined with a monomer selected from (B) epoxy, diisocyanate, polyester, and diamine in an A/B mole ratio ranging from about 2.0 to 1.05, and (b) an (A) diamine combined with a monomer selected from (B) epoxy and dianhydride or its corresponding tetraacid or diacid-diester in an A/B mole ration ranging from about 2.0 to 1.05, and mixtures thereof.

U.S. Pat. No. 5,039,417 describes a mixture made of a multi-block polymer comprising a first prepolymer comprising an imide or amic-acid made by reacting an (A) diisocyanate with (B) a dianhydride or its corresponding tetraacid or diacid-diester in an A/B mole ratio ranging from about 2.0 to 1.05, chain extended with a second different and compatible prepolymer selected from the group consisting of (a) an (A) dianhydride or its corresponding tetraacid or diacid-diester combined with a monomer selected from (B) epoxy, diisocyanate, polyester, and diamine in an A/B mole ratio ranging from about 2.0 to 1.05, and (b) an (A) diamine combined with a monomer selected from (B) epoxy, diisocyanate, and dianhydride or its corresponding tetraacid or diacid-diester in an A/B mole ratio ranging from about 2.0 to 1.05, and mixtures thereof.

U.S. Ser. No. 624,426 filed Dec. 5, 1990, describes a membrane made of a multi-block polymer comprising a first prepolymer made by combining an (A) epoxy with a (B) polyester in an A/B mole ratio ranging from about 2.0 to 1.05 to produce an ester which is chain extended with a second compatible prepolymer selected from the group consisting of (a) an (A) dianhydride or its corresponding tetraacid or diacid-diester combined with a monomer selected from (B) epoxy, diisocyanate, polyester and diamine in an A/B mole ratio ranging from about 2.0 to 1.05, and (b) an (A) diamine combined with a monomer selected from (B) epoxy, diisocyanate, and dianhydride or its corresponding tetraacid or diacid-diester in an A/B mole ratio ranging from about 2.0 to 1.05, and mixtures thereof.

U.S. Pat. No. 5,096,592 describes a membrane made of a multi-block polymer comprising a first prepolymer ester made by combining an (A) epoxy with a (B) dianhydride or its corresponding tetraacid or diacid-diester in an A/B mole ratio ranging from about 2.0 to 1.05, chain extended with a second different compatible prepolymer selected from the group consisting of (a) an (A) diisocyanate combined with a monomer selected from (B) epoxy, polyester, dianhydride or its corresponding tetraacid or diacid-diester, and diamine in an A/B mole ratio ranging from about 2.0 to 1.05, (b) an (A) dianhydride or its corresponding tetraacid or diacid-diester combined with a monomer selected from (B) diisocyanate, polyester and diamine in an A/B mole ratio ranging from about 2.0 to 1.05, and (c) an (A) diamine combined with a monomer selected from (B) epoxy, diisocyanate, and dianhydride or its corresponding tetraacid or diacid-diester in an A/B mole ratio ranging from about 2.0 to 1.05, and mixtures thereof.

U.S. Pat. No. 5,049,281 describes a membrane made of a multi-block polymer comprising a first prepolymer made by combining (A) an epoxy with (B) a diamine in an A/B or B/A mole ratio ranging from about 2.0 to 1.05, chain extended with a second, compatible prepolymer selected from the group consisting of (a) an (A) diisocyanate combined with a monomer selected from (B) epoxy, polyester, dianhydride or its corresponding tetraacid or diacid-diester, and diamine in an A/B or B/A mole ratio ranging from about 2.0 to 1.05, (b) an (A) polyester combined with (B) epoxy in an A/B or B/A mole ratio ranging from about 2.0 to 1.05, (c) an (A) dianhydride or its corresponding tetraacid or diacid-diester combined with a monomer selected from (B) epoxy, diisocyanate, polyester, and diamine in an A/B or B/A mole ratio ranging from about 2.0 to 1.05, and (d) an (A) diamine combined with a monomer selected from (B) diisocyanate and dianhydride or its corresponding tetraacid or diacid-diester in an A/B or B/A mole ratio ranging from about 2.0 to 1.05, and mixtures thereof.

U.S. Pat. No. 5,130,017 describes a membrane made of a multi-block polymer comprising a first prepolymer made by combining (A) a diamine with (B) a dianhydride or its corresponding tetraacid or diacid-diester in an A/B mole ratio ranging from about 2.0 to 1.05, to produce an amide acid prepolymer which is subsequently chain extended with a second compatible prepolymer selected from the group consisting of (A) dianhydride or its corresponding tetraacid or diacid-diester combined with a monomer selected from (B) epoxy, diisocyanate, and polyester, in an A/B mole ratio ranging from about 2.0 to 1.05 and mixtures thereof.

Any of the membranes recited above preferably those containing polyester or polyester copolymer membranes are useful in the present separation of alcohol from mixtures of alcohol and n-paraffin.

The membranes can be used in any convenient form such as sheets, tubes or hollow fibers. Sheets can be used to fabricate spiral wound modules familiar to those skilled in the art.

An improved spiral wound element is disclosed in copending application U.S. Ser. No. 07/921,892 filed Jul. 29, 1992 wherein one or more layers of material are used as the feed spacer, said material having an open cross-sectional area of at least 30 to 70% and wherein at least three layers of material are used to produce the permeate spacer characterized in that the outer permeate spaced layers are support layers of a fine mesh material having an open cross-sectional area of about 10 to 50% and a coarse layer having an open cross-sectional area of about 50 to 90% is interposed between the aforesaid fine outer layers, wherein the fine layers are the layers in the interface contact with the membrane layers enclosing the permeate spacer. While the permeate spaced comprises at least 3 layers, preferably 5 to 7 layers of alternating fine and coarse material are used, fine layers always being the outer layers. In a further improvement an additional woven or non-woven chemically and thermally inert sheet may be interposed between the membrane and the multi-layer spacers, said sheet being for example a sheet of Nomex about 1 to 15 mils thick.

Alternatively, sheets can be used to fabricate a flat stack permeator comprising a multitude of membrane layers alternately separated by feed-retentate spacers and permeate spacers. The layers are glued along their edges to define separate feed-retentate zones and permeate zones. This device is described and claimed in U.S. Pat. No. 5,104,532.

Tubes can be used in the form of multi-leaf modules wherein each tube is flattened and placed in parallel with other flattened tubes. Internally each tube contains a spacer. Adjacent pairs of flattened tubes are separated by layers of spacer material. The flattened tubes with positioned spacer material is fitted into a pressure resistant housing equipped with fluid entrance and exit means. The ends of the tubes are clamped to create separate interior and exterior zones relative to the tubes in the housing. Apparatus of this type is described and claimed in U.S. Pat. No. 4,761,229.

Hollow fibers can be employed in bundled arrays potted at either end to form tube sheets and fitted into a pressure vessel thereby isolating the insides of the tubes from the outsides of the tubes. Apparatus of this type are known in the art. A modification of the standard design involves dividing the hollow fiber bundle into separate zones by use of baffles which redirect fluid flow outside the hollow fibers of the bundle and prevent fluid channelling and polarization on the outside hollow fibers. This modification is disclosed and claimed in U.S. Ser. No. 423,178 filed Oct. 18, 1989, now U.S. Pat. No. 5,108,605.

Preferably the direction of flow in a hollow fiber element will be counter-current rather than co-current or even transverse. Such counter-current flow can be achieved by wrapping the hollow fiber bundle in a spiral wrap of flow-impeding material. This spiral wrap extends from a central mandrel at the center of the bundle and spirals outward to the outer periphery of the bundle. The spiral wrap contains holes along the top and bottom ends whereby fluid entering the bundle for flow outside the hollow fibers at one end is partitioned by passage through the holes and forced to flow parallel to the hollow fibers down the channel created by the spiral wrap. This flow direction is counter-current to the direction of flow inside the hollow fibers. At the bottom of the channels the fluid re-emerges from the hollow fiber bundle through the holes at the opposite end of the spiral wrap and is directed out of the module. This device is disclosed and claimed in copending application U.S. Ser. No. 802,158 filed Dec. 4, 1991.

As previously stated separation is preferably performed under pervaporation conditions, most preferably pervaporation operation at atmospheric pressure on the permeate side of the membrane at elevated temperature.

The preferred membranes employed in the present invention are generally described as polyimide/aliphatic polyester copolymer membranes and are described and claimed in U.S. Pat. No. 4,944,880 and U.S. Pat. No. 4,990,275.

The polyimide/aliphatic polyester copolymer membranes are made from copolymers comprising polyimide segments and oligomeric aliphatic polyester segments, the polyimide being derived from a dianhydride having between 8 and 20 carbons and a diamine having between 2 and 30 carbons and the oligomeric aliphatic polyester being a polyadipate, a polysuccinate, a polymalonate, a polyoxalate or a polyglutarate. Alternately, an activated anhydride acid chloride such as trimellitic anhydride acid chloride may be used instead of a dianhydride.

The diamines which can be used include phenylene diamine, methylene dianiline (MDA), methylene di-o-chloroaniline (MOCA), methylene bis(dichloroaniline) (tetrachloro MDA), methylene dicyclohexylamine ($H_{12}$-MDA), methylene dichlorocyclohexylamine ($H_{12}$-MOCA), methylene bis(dichlorocyclohexylamine) (tetrachloro $H_{12}$-MDA), 4,4'(hexafluoroisopropylidene)-bisaniline (6F diamine), 3,3'-diaminophenyl sulfone (3,3' DAPSON), 4,4'-diaminophenyl sulfone (4,4' DAPSON), 4,4'-dimethyl-3,3'-diaminophenyl sulfone (4,4'-dimethyl-3,3' DAPSON), 2,4-diamino cumene, methyl bis(di-o-toluidine), oxydianiline (ODA), bisaniline A, bisaniline M, bisaniline P, thiodianiline, 2,2-bis[4-(4-aminophenoxy) phenyl] propane (BAPP), bis [4-(4-aminophenoxy)phenyl] sulfone (BAPS), 4,4'-bis(4-aminophenoxy)biphenyl (BAPB), 1,4-bis(4-aminophenoxy)benzene (TPE-Q), and 1,3-bis(4-aminophenoxy)benzene (TPE-R).

The dianhydride is preferably an aromatic dianhydride and is most preferably selected from the group consisting of pyromellitic dianhydride, 3,3',4,4'-benzophenone betracarboxylic dianhydride, 4,4'-(hexafluoroisopropylidene)-bis(phthalic anhydride), 4,4'-oxydiphthalic anhydride, diphenylsulfone-3,3',4,4'-tetracarboxylic dianhydride, and 3,3'4,4'-biphenyl-tetracarboxylic dianhydride.

Examples of preferred polyesters include polyethyleneadipate and polyethylenesuccinate.

The polyesters used generally have molecular weights in the range of 500 to 5000, preferably 1000 to 2000.

In practice the membrane may be synthesized as follows. One mole of a polyester, e.g., polyadipate, polysuccinate, polyoxalate, polyglutarate or polymalonate, preferably polyethyleneadipate or polyethylenesuccinate, is reacted with two moles of a dianhydride, e.g., pyromellitic dianhydride, with stirring for about 5 hours at about 170° C. to make a prepolymer in the end-capping step. One mole of this prepolymer is then reacted with one mole of diamine, e.g., methylene di-o-chloroaniline (MOCA) to make a copolymer. Finally, heating of the copolymer at 260°-300° C. for about 10 minutes leads to the copolymer containing polyester segments and polyimide segments. The heating step converts the polyamic acid to the corresponding polyimide via imide ring closure with removal of water.

In the synthesis an aprotic solvent such as dimethylformamide (DMF) is used in the chain-extension step. DMF is a preferred solvent but other aprotic solvents are suitable and may be used. A concentrated solution of the polyamic acid/polyester copolymer in the solvent is obtained. This solution is used to cast the membrane. The solution is spread on a glass plate or a high temperature porous support backing, the layer thickness being adjusted by means of a casting knife. The membrane is first dried at room temperature to remove most of the solvent, then at 120° C. overnight. If the membrane is cast on a glass plate it is removed from the casting plate by soaking in water. If cast on a porous support backing it is left as is. Finally, heating the membrane at 260°-300° C. for about 10 minutes results in the formation of the polyimide. Obviously, heating at 260°-300° C. requires that if a backing is used the backing be thermally stable, such as teflon, fiber glass, sintered metal or ceramic or high temperature polymer backing.

Figure 1:
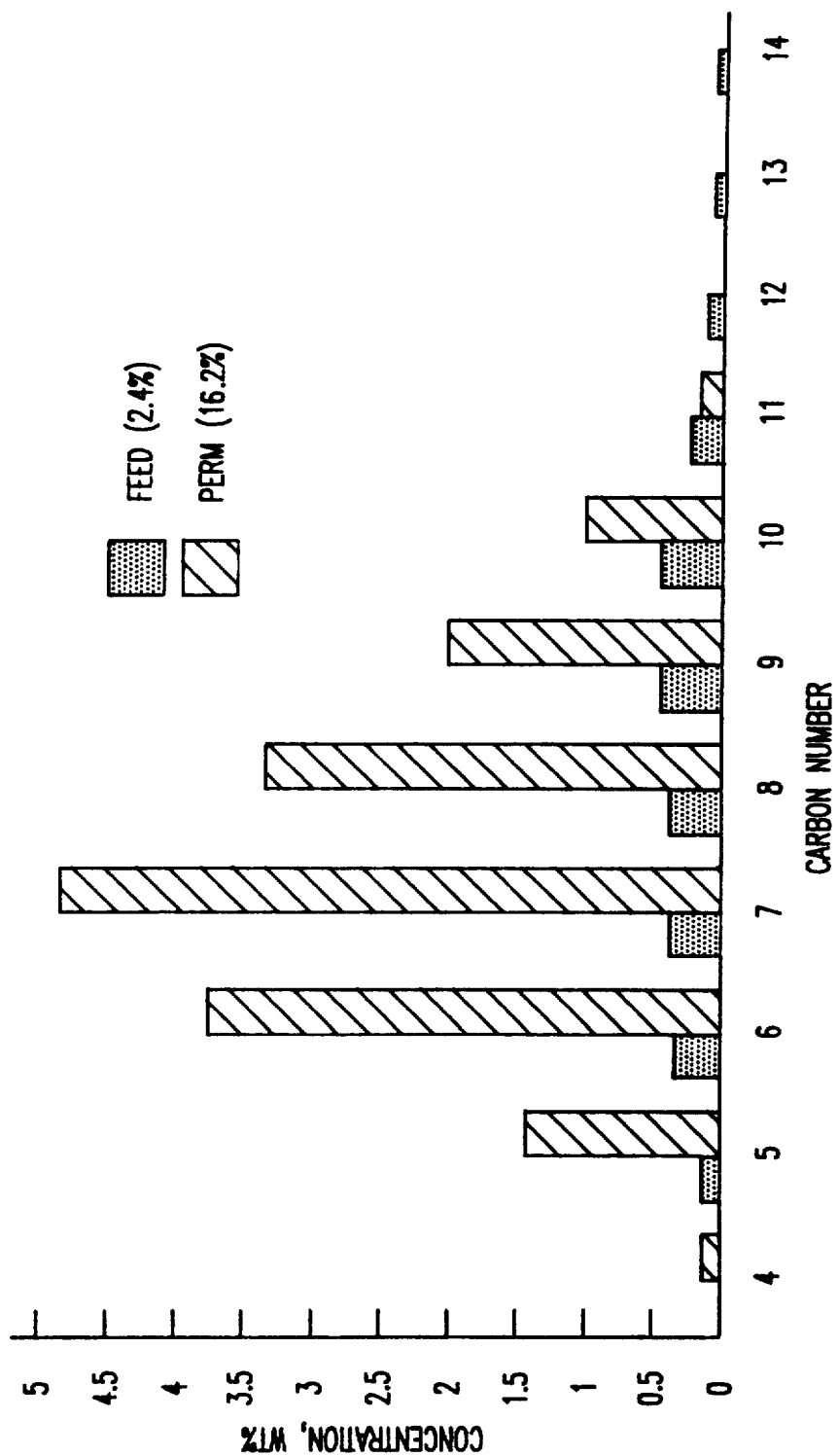
FIG. 1 shows alcohol separation through a polyimide/polysuccinate membrane conducted at 170° C. and 5 mm Hg.

The invention is further demonstrated by the following non-limiting examples.

The light oil product with a boiling point in the 240°-550° F. range from the Fischer-Tropsch synthesis process was subjected to pervaporation at 170° C. and 5 mm Hg permeate pressure using a polyimide/polysuccinate membrane.

The membrane was made as follows:

To 1.31 g (0.006 mole) or pulverized pyromellitic dianhydride (PMDA) under $N_2$ in a 250 ml reactor was added 5 g (0.003 mole) of polyethylene succinate (PES) diol with a molecular weight of about 1670. The reactor content was heated to 170° C. and maintained at this temperature for about 5.75 hours with stirring at 400 rpm. This completed the end-capping reaction of PES with PMDA. To the end-capping reaction product was added 20 g of dimethylformamide (DMF), and the temperature was dropped to about 70° C. with stirring for about 0.5 hour. To the reactor content was added 0.8 g (0.003 mole) of methylene di-o-chloroaniline (MOCA) in 5 g DMF solution. The solution was stirred at 70° C. for about 1.5 hours, and DMF was added to keep up with the viscosity increase of the solution during the chain-extension reaction of the end-capped product with MOCA. In this chain-extension reaction, about 206 g DMF was added, and the viscosity increase indicated the occurrence of this reaction. The solution was then cooled to room temperature. The resulting solution containing about 3 wt. % of the copolymer with polyamic acid and polyethylenesuccinate segments had suitable consistency for solution casting in the preparation of membranes.

The resulting solution was centrifuged for about 5 minutes. Following centrifugation, a membrane was knife-cast onto a microporous Teflon support (Gore-Tex with a pore size of about 0.2 micron, a porosity of about 80%, and a thickness of about 50 microns) with a knife gap setting of about 24 mils. DMF was allowed to evaporate from the membrane in a nitrogen purge oven at 70° C. in a hood over a period of about 24 hours. This drying avoids the crystallization of polyethylenesuccinate segments and thus the brittleness problem of the membrane. The membrane was further dried at 120° C. for about 20 hours to remove the residual DMF solvent. Finally, the membrane was cured to convert the polyamic acid to polyimide with removal of water by heating from room temperature to 260° C., maintaining at this temperature for 10 minutes, and cooling to room temperature. The resulting membrane had a thickness of about 12 microns (excluding the support).

The flux at 170° C. was 19 kg/m$^2$ day which is quite good considering that the membrane was 12 microns thick. Flux can be increased by using a thinner membrane and/or by increasing the operating temperature. Overall alcohol/paraffin selectivity was 7.8. Selectivity for individual alcohols is presented in FIG. 1. Selectivity is highly dependent on the carbon number of the alcohol. For the lower carbon number alcohols ($C_4$-$C_7$) alcohol concentrations in the permeate ranged from under 0.5 wt. % for $C_4$ to over 4.5 wt. % for $C_7$. The $C_7$ alcohol/non-alcohol selectivity was 12.3. The selectivity was calculated by ratioing the permeate alcohol/non-alcohol ratio to the feed alcohol/non-alcohol ratio. The higher carbon number alcohols ($C_8$-$C_{11}$) showed lower selectivities which may be attributable to their not being completely vaporized at the 170° C. operating temperature. Higher selectivity may be secured by operating at higher temperature, e.g., 200° C.+.

What is claimed is:

1. A method for separating n-$C_1$-$C_{20}$ alcohols from feed mixtures comprising said alcohols with n-paraffins said method comprising contacting said mixture with one side of a dense film, non-porous membrane under pervaporation conditions to effect the separation and recovering a permeate enriched in alcohol content as compared to the feed mixture and recovering a retentate lean in alcohol content as compared to the feed mixture.

2. The method of claim 1 wherein the alcohol recovered is an n-$C_4$-$C_{14}$ alcohol.

3. The method of claim 2 wherein the alcohol recovered is an n-$C_6$-$C_{11}$ alcohol.

4. The method of claim 1 wherein the membrane used is a polyester containing membrane.

5. The method of claim 1 wherein the alcohol concentration in the alcohol/n-paraffin mixture is in the range 0.5 to 99.5% alcohol.

6. The method of claim 1 wherein the membrane used is a polyimide/aliphatic polyester copolymer membrane.

* * * * *